Figure 4:
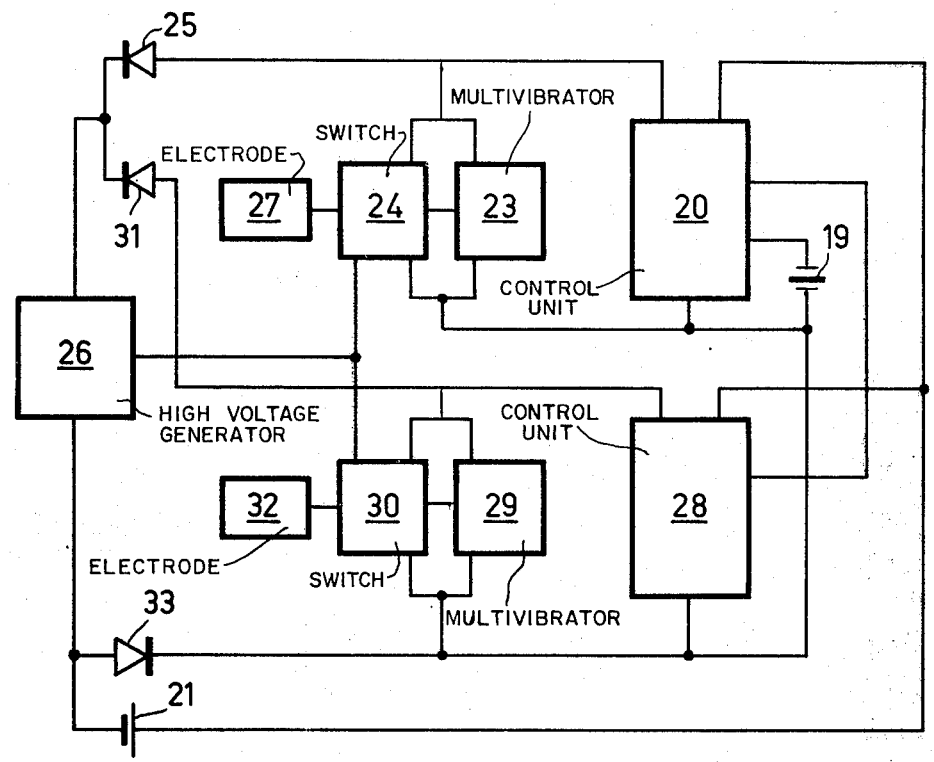

United States Patent [19]

Vredenbregt et al.

[11] 3,941,137

[45] Mar. 2, 1976

[54] AMBULATORY STIMULATOR

[75] Inventors: Jakob Vredenbregt; Antonius Maria Klomp; Adrianus Cornelis Maria Hurkmans, all of Eindhoven, Netherlands

[73] Assignee: U.S. Philips Corporation, New York, N.Y.

[22] Filed: Feb. 24, 1972

[21] Appl. No.: 228,912

[30] Foreign Application Priority Data
Feb. 27, 1971 Netherlands.................... 7102659

[52] U.S. Cl............................. 128/423 R; 128/411
[51] Int. Cl.²........................................... A61N 1/36
[58] Field of Search......... 128/419 C, 419 E, 419 P, 128/419 R, 421, 422, 423, 404, 411, 416, 417, 418; 200/86.5, DIG. 35, 61.89, 81 R, 81 H, 83 R, 83 Z; 340/279, 272, 273, 278, 240

[56] References Cited
UNITED STATES PATENTS

| | | | |
|---|---|---|---|
| 1,096,125 | 5/1914 | Pidot................................. | 128/423 |
| 2,290,387 | 7/1942 | Schwartz............................ | 128/2 S |
| 2,590,876 | 4/1942 | Landauer........................... | 128/417 |
| 2,842,136 | 7/1958 | Browner............................ | 128/422 |
| 3,017,497 | 1/1962 | Albright............................. | 200/86.5 |
| 3,085,577 | 4/1963 | Berman et al. .................... | 128/418 |
| 3,111,721 | 11/1963 | Montague, Jr.................... | 200/86.5 |
| 3,204,637 | 9/1965 | Frank et al. ...................... | 128/423 |
| 3,659,615 | 5/1972 | Enger................................ | 128/419 P |
| 3,693,627 | 9/1972 | Berkovits.......................... | 128/419 P |

FOREIGN PATENTS OR APPLICATIONS

| | | | |
|---|---|---|---|
| 6,717,637 | 6/1969 | Netherlands....................... | 128/423 |

OTHER PUBLICATIONS

"Radio–Electronics", Vol. 36, No. 6, June, '65, p. 29.

*Primary Examiner*—William E. Kamm
*Attorney, Agent, or Firm*—Frank R. Trifari

[57] ABSTRACT

An electro-therapeutic apparatus for stimulation of the locomotive nerves enables activation of both legs in a locomotive cycle by means of pressure impulses originating from a pressure-sensitive medium provided underneath the ball of one of the feet. A pressure-cell which is closed by a bimorph plate of piezoelectric material is used as the switching element for converting pressure impulses into electric pulses.

1 Claim, 6 Drawing Figures

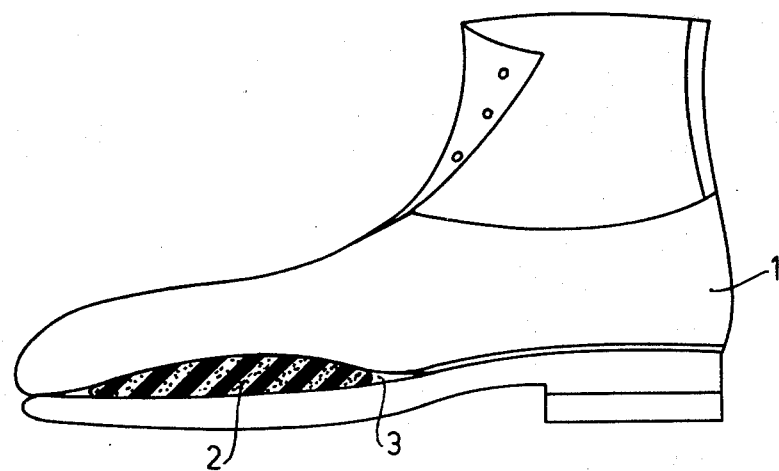
Fig.1
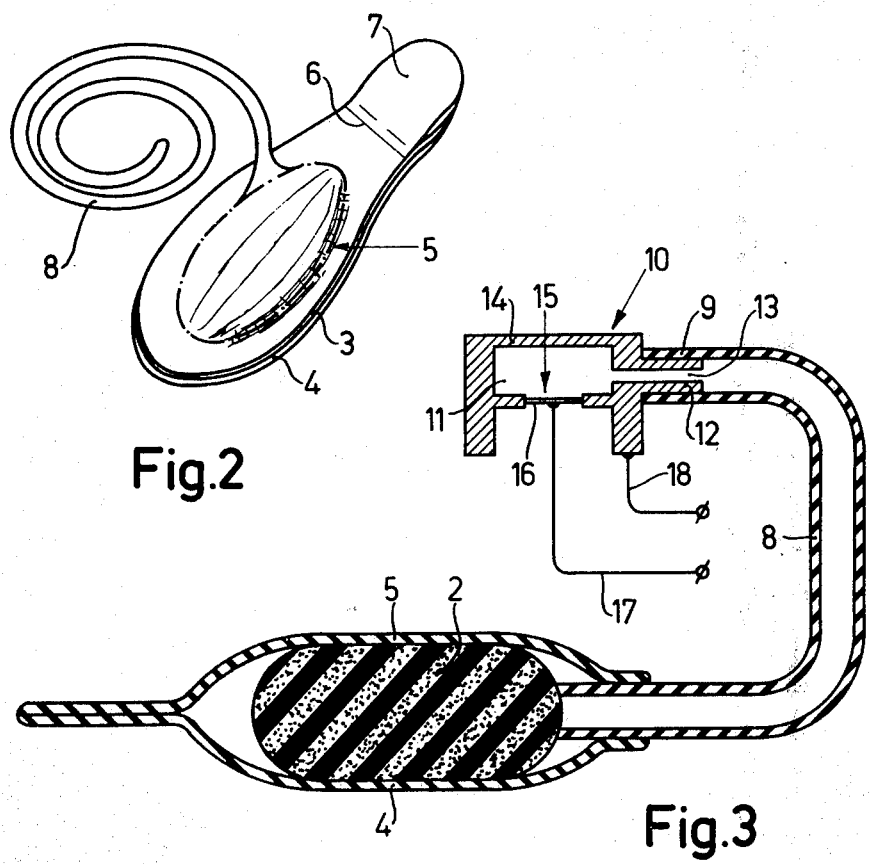
Fig.2
Fig.3

AMBULATORY STIMULATOR

The invention relates to an electro-therapeutic apparatus for the stimulation of locomotive organisms whose natural impulses function inadequately. Such an apparatus has a switching element, a stimulator and a pressure-sensitive mechanism to be provided underneath the ball of a foot.

An apparatus of this kind is known from applicants' copending U.S. patent application Ser. No. 115,786 filed Feb. 16, 1971 how U.S. Pat. No. 3,881,496. In an apparatus described therein a single stimulator is activated from a pressure-sensitive mechanism. For diplegia patients this apparatus has the drawback that two separate apparatuses have to be carried. Each of these two apparatuses requires an amount of energy which is to be supplied by portable energy sources. Moreover, it is necessary that the operation of both apparatuses is substantially identical as otherwise the regularity in the locomotive pattern is disturbed. Consequently, it is desirable to realize an apparatus by means of which a stimulator can be activated for each leg from a single pressure-sensitive mechanism, and which combines low energy consumption with a high degree of reliability in prolonged regular operation. The object of the invention is to meet these requirements and to this end an electro-therapeutical apparatus of the kind set forth is characterized in that stimulatory electrodes for both legs can be periodically activated by means of impulses originating from a pressure-sensitive mechanism underneath one of the feet.

A single electro-therapeutic apparatus according to the invention also suffices for diplegia patients, the apparatus, obviously, comprising at least two stimulatory electrodes. Hemiplegia patients can carry the pressure-sensitive mechanism underneath the healthy leg so that a normal locomotive pattern is better approximated during walking. The regularity in the locomotive pattern is then co-determined to a large extent by an electronic control circuit. To this end, this circuit must be accurately adjustable and must have a stable operation during a prolonged period. It is necessary that the pressure-sensitive mechanism as well as the switching element have a high degree of reliability and sensitivity. To this end, the pressure-sensitive mechanism in a preferred embodiment according to the invention comprises an elastic material provided with open ducts, which is connected to the switching element by means of a hose extending therefrom. The switching element is preferably activated by locally occurring pressure gradients and is, for example, insensitive to the nominal value of the gas pressure in the pressure-sensitive mechanism. To this end, the switching element may be provided, for example, with a material having piezoelectric properties so that pressure impulses generated in the pressure-sensitive mechanism are directly converted into electric voltage pulses for controlling and activating stimulator circuits.

When a patient does not wish to walk, it is annoying that the stimulations continue. In a preferred embodiment the necessity of having to switch the apparatus continuously on and off is eliminated by providing the apparatus with an electronic circuit such that the apparatus ceases stimulation, for example, 2 seconds after a last pressure impulse, and becomes active again only after a next pressure impulse has been administered.

In order to save energy, it is advantageous to stimulate not the ambulatory muscles themselves, but rather the nerves activating the ambulatory muscles. As a result, a smaller energy suffices so that the patients are also less liable to suffer from pain.

Figure 5:
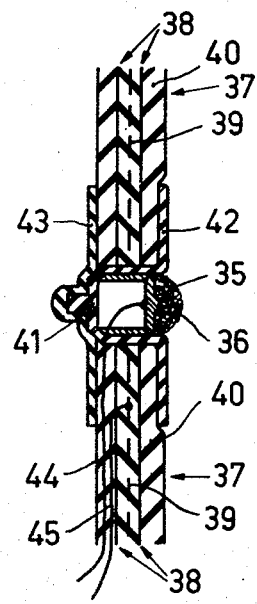

In order that the invention may be readily carried into effect, some embodiments thereof will now be described in detail, by way of example, with reference to the accompanying diagrammatic drawings, in which:

FIG. 1 shows a shoe provided with a pressure-sensitive medium in the form of an insert sole, FIG. 2 shows a loose insert sole as used in the shoe shown in FIG. 1, FIG. 3 shows a pressure-sensitive mechanism in which the switching element contains a plate of piezoelectric material, FIG. 4 shows an electronic circuit for controlling two stimulators in which a piezoelectric switch is used, FIG. 5 shows an electrode for stimulation of ambulatory nerves via the skin.

Figure 6:
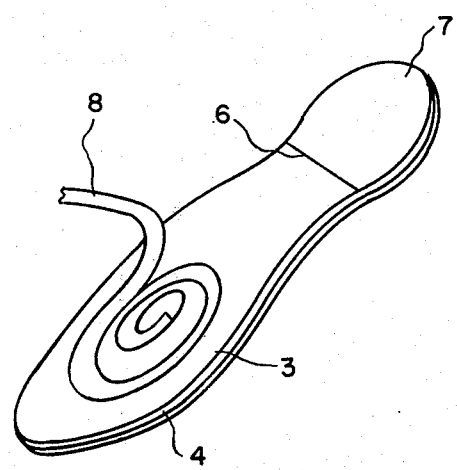

FIG. 6 is a perspective view showing another type of pressure sensitive mechanism.

Provided in a shoe 1 at the area of the ball of the foot is a pressure-sensitive medium 2 which is preferably enclosed in a loose inert sole 3. The pressure-sensitive medium consists of a spongy material having open ducts, but may also be formed by, for example, a coiled hose which is closed in the centre of the coil or is folded at that area as shown in FIG. 6. The insert sole 3 which is separately shown in FIG. 2 consists of a lower cover layer 4 and an upper cover layer 5. The upper cover layer preferably consists of two portions which are separated at a separating line 6, so that the insert sole can be adapted to the shoe size by displacement of a rear portion 7. The cover layers have a tough flexibility such that motions of the foot outside the locomotive pattern exert no effect on the pressure-sensitive medium whilst locomotive motions, i.e. the weight of the body bearing on the sole, compress the pressure-sensitive medium with a very high degree of reliability. As is shown in FIG. 3, the pressure-sensitive medium is connected to a switching element 10 by means of a hose 8. As a result, variations in the volume of the pressure-sensitive medium are converted into pressure impulses which are applied to the switching element. If a coiled hose is used as the pressure-sensitive medium, the connecting hose 8 may be formed by a portion of this hose, and in the case of a folded hose, the connecting hose may also be a double hose.

In a preferred embodiment of a switching element as shown in FIG. 3, the connecting hose 8 is closed at an end remote from the pressure-sensitive medium by a pressure cell 11. The pressure cell 11 is formed by a wall portion 12 which can be connected to the hose 8 and which has an aperture 13, and a box-shaped wall portion 14 having an aperture 15. The aperture 15 is closed by a plate of piezoelectric material 16. Connected to the piezoelectric plate 16 is an electrically conducting wire 17, whilst an electrically conducting wire 18 is connected to an electrically conducting cell wall 14. Via these electric conductors electric pulses, generated by pressure impulses exerted on the piezoelectric plate, can be applied as control pulses to a control circuit for a stimulator.

FIG. 4 shows a block diagram of a preferred circuit for control and activation of two stimulators from a single pressure-sensitive medium. In this circuit electric pulses originating from a piezoelectrical switching element 19 are applied to a first control unit 20 which produces pulses to stimulate electrode 27 and for producing a switching pulse to a second control unit 28. The voltage of a supply battery 21, for example, consisting of a 22.5 volts battery, is then available to a low-frequency multivibrator 23, to a high-voltage switch 24 and, via a diode 25, to a high-voltage generator 26, so that a first leg electrode 27 starts to supply stimulatory pulses. After disappearance of the electric pulse of the piezoelectric switching element 19, or because the leg under which the pressure-sensitive medium is situated is lifted, or after an electronically controllable switching time of, for example, 2 seconds, a switching pulse is applied from the control unit 20 to a control unit 28 to produce pulses for stimulatory electrode 32. The battery voltage then becomes available to a second low-frequency multivibrator 29, to a second high-voltage switch 30 and, via a diode 31, to the high voltage-generator 26 so that a second leg electrode 32 starts to supply stimulatory pulses. The diodes 25, 31 and 33 prevent destruction of the equipment in the case of incorrect connection of the supply battery 21, the diodes 25 and 31 also serving as control gates. In the rest state, the described circuit consumes a very small current of, for example, a few microamperes. The leg electrodes 27 and 32 supply, for example, voltage pulses which can be controlled from 0 to 100 volts with a repetition frequency of 50 Hz and a pulse duration of approximately 400 microseconds, the maximum output current being approximately 6 mA.

FIG. 5 is a cross-sectional view of a preferred embodiment of a leg electrode. Shown is a central electrode 35 which makes electrical contact with the skin, for example, via a moisture-holding sponge 36 drenched in water or electrode paste. A second electrode 37 is made of an electrically conducting gauze 39 having an area of, for example, approximately 15 cm² and being embedded in elastic material 38 about the central electrode 35. At the side facing the skin the elastic material 38 consists of conducting material, for example, a conducting rubber material 40. This construction of the electrode produces a favourable electrical contact with the skin over a comparatively large area (15 cm²), so that favourable nerve activation can be accompanied by a minimum of irritation to the patient. An insulating bush 41 having flanges 42 and 43 provides proper insulation between the central electrode 35 and the second electrode 37. The electrical supply leads 44 and 45, also embedded in the rubber material, provide the supply of the stimulatory pulses and are preferably connected to the switching element by means of an asymmetrical plug.

What is claimed is:

1. An electro-therapeutic apparatus for the stimulation of locomotive organisms which normally function inadequately comprising a pressure-sensitive mechanism located underneath the ball of a foot of one of the legs of the patient for producing periodic pressure pulses, a switching element connected with said mechanism being activated by said pressure pulses from said mechanism for producing electric pulses, stimulator means connected to said switching element having a stimulatory electrode carried on each leg of the patient each being periodically activated by said electric pulses in response to said pressure pulses originating from said pressure sensitive mechanism, said electrodes comprising a central electrode element, a second electrode surrounding said central electrode, insulating means provided between said central and second electrodes, said second electrode being made of an electrically conducting gauze, and an electrically conducting rubber element for providing contact between said second electrode and the skin of the patient.

* * * * *